(12) United States Patent
Arao

(10) Patent No.: US 11,099,162 B2
(45) Date of Patent: Aug. 24, 2021

(54) METHOD FOR ANALYZING ACTIVE INGREDIENTS OF CANNABIS AND CONTROL PROGRAM FOR LIQUID CHROMATOGRAPH

(71) Applicant: SHIMADZU CORPORATION, Kyoto (JP)

(72) Inventor: Yohei Arao, Hanover, MD (US)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 16/338,208

(22) PCT Filed: Aug. 3, 2017

(86) PCT No.: PCT/US2017/045223
§ 371 (c)(1),
(2) Date: Mar. 29, 2019

(87) PCT Pub. No.: WO2018/063498
PCT Pub. Date: Apr. 5, 2018

(65) Prior Publication Data
US 2020/0025728 A1 Jan. 23, 2020

Related U.S. Application Data

(60) Provisional application No. 62/402,089, filed on Sep. 30, 2016.

(51) Int. Cl.
*G01N 30/04* (2006.01)
*G01N 30/74* (2006.01)
(Continued)

(52) U.S. Cl.
CPC ............. *G01N 30/74* (2013.01); *C07C 39/08* (2013.01); *C07D 311/80* (2013.01); *G16C 20/20* (2019.02); *G01N 2030/027* (2013.01)

(58) Field of Classification Search
CPC .. G01N 30/74; G01N 2030/027; G16C 20/20; C07C 39/08; C07D 311/80
See application file for complete search history.

(56) References Cited

U.S. PATENT DOCUMENTS 5,968,361 A 10/1999 Goetzinger et al.
2008/0096922 A1* 4/2008 Ban ...................... C07C 311/18
514/317

(Continued)

FOREIGN PATENT DOCUMENTS

JP 2015-052570 A 3/2015
WO 2006/090428 A2 8/2006

OTHER PUBLICATIONS

Communication dated Sep. 11, 2019, from the European Patent Office in counterpart European Application No. 17856967.9.
(Continued)

*Primary Examiner* — David P Porta
*Assistant Examiner* — Mamadou Faye
(74) *Attorney, Agent, or Firm* — Paratus Law Group, PLLC

(57) ABSTRACT

In an LC system using an ODS column (15) and UV detector (17), a cannabis-derived sample is analyzed by gradient elution using a phosphoric acid aqueous solution and phosphoric-acid-containing methanol. A control unit (3) regulates the openings of solenoid valves in a mixer (12) so that the increase rate of the mixture ratio of the phosphoric-acid-containing methanol in a second part of the analysis period is higher than in a first part. By this operation, ten active ingredients (including Total THC, Total CBD and CBN) contained in cannabis can be satisfactorily separated within an analysis time which is equal to or even shorter than approximately 30 minutes. Each ingredient separated by the column (15) is detected by the UV detector (17). An active ingredient identification processor (22) identifies the ten
(Continued)

active ingredients based on the retention times of the peaks on a chromatogram created from the detection signals.

10 Claims, 2 Drawing Sheets

(51) Int. Cl.
    *G16C 20/20*     (2019.01)
    *C07C 39/08*     (2006.01)
    *C07D 311/80*     (2006.01)
    *G01N 30/02*     (2006.01)

(56) References Cited

U.S. PATENT DOCUMENTS

| | | | |
|---|---|---|---|
| 2012/0015057 A1* | 1/2012 | Ohishi | A61P 3/06 424/729 |
| 2015/0297653 A1 | 10/2015 | Speier | |

OTHER PUBLICATIONS

T. Lehmann, et al., "High Performance Liquid Chromatographic Profiling of Cannabis Products", Journal of Liquid Chromatography, Mar. 1, 1995, vol. 18, No. 4, pp. 689-700 (12 pages total).

Tri J Raharjo, et al., "Methods for the Analysis of Cannabinoids in Biological Materials: a Review", Phytochemical Analysis, Mar. 22, 2004, vol. 15, pp. 79-94 (16 pages total).

Christian Lindholst, "Long term stability of cannabis resin and cannabis extracts", Australian Journal of Forensic Sciences, Sep. 2010, pp. 181-190, vol. 42, No. 3.

Written Opinion for PCT/US2017/45223, dated Oct. 16, 2017.

International Search Report for PCT/US2017/45223, dated Oct. 16, 2017.

* cited by examiner

METHOD FOR ANALYZING ACTIVE INGREDIENTS OF CANNABIS AND CONTROL PROGRAM FOR LIQUID CHROMATOGRAPH

CROSS REFERENCE TO RELATED APPLICATIONS

This Application is a National Stage of International Application No. PCT/US2017/045223 filed Aug. 3, 2017, claiming priority based on U.S. Patent Application No. 62/402,089 filed Sep. 30, 2016.

TECHNICAL FIELD

The present invention relates to an analysis method for the identification and/or quantitative determination of active ingredients contained in cannabis, as well as a computer program for controlling a liquid chromatograph for such an analysis. It should be noted that the term "cannabis" in the present description includes various forms of *Cannabis sativa*, such as the corolla or leaves of hemp (marijuana) in an unprocessed form, those in a dried form, as well as their extractives that are processed into a resin or liquid form.

BACKGROUND ART

While cannabis is banned by law in many countries including Japan, there are some countries in which its use is legalized, such as the Netherlands and Brazil. In the United States of America, its use has been legalized in some states for medical purposes only. An extremely small number of states have even legalized the use of cannabis for tasting purposes as well as for medical purposes. There are also some reports stating that cannabis is far less toxic or less addictive than other kinds of drugs. Its effects as a medical agent have also been widely recognized. Accordingly, despite the fact that many people are still against the removal of the existing ban, the general trend in the USA is toward the legalization of cannabis.

It has been commonly known that cannabis contains various compounds, which are generally called "cannabinoids", which can act as active ingredients having pharmacological effects on human bodies. The kinds and amounts of active ingredients contained in cannabis vary depending on such conditions as the origin of the marijuana and its planting conditions (e.g. the kinds and/or amounts of fertilizers, growing season, and so on). Accordingly, in the American states in which cannabis is legalized, it has been necessary to accurately identify active ingredients contained in cannabis and determine their quantities. There are many commissioned analytical institutions undertaking such tests and analyses. However, at present, no official method is specified, and no analysis method has yet been established. The current situation is such that commissioned analytical institutions (or similar organizations) need to individually determine analysis methods by trial and error. Therefore, the analysis is not always highly reliable. It is also difficult to compare analysis results provided by different commissioned analytical institutions.

In general, gas chromatographs (GC), gas chromatograph mass spectrometers (GC-MS), liquid chromatographs (LC), liquid chromatograph mass spectrometers (LC-MS) and various other analyzing devices have been used for the testing and analysis of active ingredients of cannabis.

GC-MS and LC-MS have also been often used for the identification of such substances as illegal drugs (e.g. synthetic cannabinoids) and toxicants (for example, see Patent Literature 1). In an analysis using a GC-MS or LC-MS, even when there are a plurality of compounds which have been incompletely separated by the GC or LC, i.e. even when the sample which has undergone the separation process by the GC or LC contains an active ingredient and foreign substance mixed together or a plurality of active ingredients mixed together, the mass spectrometer serving as the detector can separate those components according to their mass-to-charge ratios and detect each component. Such an analysis has the advantage that a number of active ingredients can be assuredly separated, and each component can be accurately detected.

However, as compared to GC or LC, GC-MS and LC-MS are considerably expensive. In general, commissioned analytical institutions make a profit by efficiently operating a number of devices. For such institutions, the cost of introducing an expensive device will impose a considerable amount of financial burden. Another problem is that GC-MS and LC-MS are more complex in operation and manipulation than GC or LC, so that they cannot be easily operated by workers who are not familiar with these analyzing tasks. In comparison with GC-MS or LC-MS, GC and LC are considerably less expensive as well as easier to operate and manipulate. However, they are also less capable of separating a plurality of compounds. Therefore, it is difficult to analyze, at one time, a large number of active ingredients contained in cannabis. For an identification and quantitative determination of a large number of active ingredients, it is normally necessary to perform a plurality of analyses under different analysis conditions. Therefore, the analysis requires a considerable amount of time, so that the analyzing efficiency is low.

CITATION LIST

Patent Literature

Patent Literature 1: JP 2015-52570 A

SUMMARY OF INVENTION

Technical Problem

The present invention has been developed to solve the previously described problems. Its objective is to provide a method for analyzing the active ingredients of cannabis, as well as a control program for the same method, by which an accurate identification and quantitative determination of a plurality of particularly important ingredients among the active ingredients of cannabis can be performed using a device that is comparatively inexpensive as well as easy to manipulate and operate.

Solution to Problem

The present invention developed for solving the previously described problems is a method for analyzing a plurality of active ingredients contained in cannabis using a liquid chromatograph, the method including:

a) a separation step, in which a plurality of components contained in a liquid sample are separated from each other by gradient elution using an ODS column as a column, with a phosphoric acid aqueous solution and phosphoric-acid-containing methanol as mobile phases;

b) a detection step, in which each component separated in the separation step is detected with a detector which is either an ultraviolet spectrometric detector or photodiode array detector; and c) an identification step, in which a plurality of predetermined active ingredients are identified based on the retention times of the peaks observed on a chromatogram created based on a detection result obtained in the detection step.

In the method for analyzing the active ingredients of cannabis according to the present invention, a plurality of components in a liquid sample are separated from each other by reversed-phase liquid chromatography in the separation step. In the detection step, the separated components are detected with a detector which is either an ultraviolet spectrometric detector or photodiode array detector. That is to say, in the detector, the absorbance of a specific wavelength of light by the component in the eluate from the column is measured to obtain detection signals corresponding to the concentration of that component. In the identification step, a chromatogram is created based on the detection result obtained with the detector, to eventually identify a plurality of specific active ingredients based on the retention times of the peaks observed on the chromatogram.

The predetermined active ingredients to be identified in the analysis method of the active ingredients of cannabis according to the present invention may include the following ten ingredients: tetrahydrocannabivarin (THCV), cannabidiol (CBD), cannabigerol (CBG), cannabidiolic acid (CBDA), cannabigerolic acid (CBGA), cannabinol (CBN), $\Delta$9-tetrahydrocannabinol (d9-THC), $\Delta$8-tetrahydrocannabinol (d8-THC), cannabichromene (CBC), and $\Delta$9-tetrahydrocannabinolic acid A (THCA-A).

While active ingredients of cannabis other than the ten aforementioned ones are also known, it is the quantitative determination of Total THC (d9-THC, d8-THC and THCA-A), Total CBD (CBD and CBDA) and CBN that is particularly in high demand for analysis. A method capable of analyzing the ten aforementioned ingredients can completely cover these highly demanded ingredients as well as exhaustively cover the ingredients designated as analysis targets in three or more organizations among the major commissioned analytical institutions in the USA.

Some active ingredients of cannabis easily undergo thermal decarboxylation. Specifically, THCA-A turns into d9-THC by thermal decarboxylation, while CBDA turns into CBD by thermal decarboxylation. In the case of a gas chromatograph, the liquid sample to be supplied to the column is normally vaporized in a sample vaporization chamber maintained at high temperatures, in which process at least some of the aforementioned active ingredients may possibly be decomposed and tower the preciseness of the quantitative determination. By comparison, the method for analyzing the active ingredients of cannabis according to the present invention, which uses a liquid chromatograph, does not cause the aforementioned kind of thermal denaturing or modification of active ingredients in the sample, so that a precise identification and quantitative determination can be performed even for ingredients that easily undergo thermal decarboxylation.

Some of the ten aforementioned ingredients have considerably similar chemical structures and accordingly have close retention times. Normally, it is difficult to completely separate those ingredients (i.e. with a degree of separation of 1 or higher). In particular, d9-THC and d8-THC, which are considerably similar in chemical structure, have been difficult to be detected in a completely separated form. This problem can be solved by the method for analyzing the active ingredients of cannabis according to the present invention; the ten aforementioned ingredients can be satisfactorily separated from each other by combining an ODS column with an appropriate gradient elution using a phosphoric acid aqueous solution and phosphoric-acid-containing methanol as the mobile phases. This means that a single analysis is enough to identify the ten aforementioned ingredients and determine the presence or absence of each ingredient. Furthermore, for example, the quantity of each ingredient can be precisely determined based on the area value of a peak on a chromatogram.

In the method for analyzing the active ingredients of cannabis according to the present invention, the mixture ratio of the phosphoric-acid-containing methanol in the gradient elution in the separation step may preferably be changed so that the mixture ratio is increased at a first increase rate and subsequently at a second increase rate which is higher than the first increase rate.

More specifically, the method for analyzing the active ingredients of cannabis according to the present invention can be performed so that at least two ingredients, i.e. THCV and CBD, are separated from each other and sequentially eluted from the column within the period of time where the mixture ratio of the phosphoric-acid containing methanol is being increased at the first increase rate, whereas seven ingredients, i.e. CBDA, CBGA, CBN, d9-THC, d8-THC, CBC and THCA-A are separated from each other and sequentially eluted from the column within the period of time where the mixture ratio of the phosphoric-acid containing methanol is being increased at the second increase rate. As for CBG, the elution from the column can be made to occur within the period of time where the mixture ratio of the phosphoric-acid containing methanol is being increased at the first increase rate, within the period of time where the mixture ratio is being increased at the second increase rate, or within a period of time overlapping the two aforementioned periods of time.

By the two-stage setting of the changing rate of the mixture ratio of the mobile phases during the gradient elution, the ten aforementioned ingredients can be satisfactorily separated, and the elution of each ingredient from the column can be quickly completed. Therefore, the analysis time can be reduced. As will be described later, an experiment conducted by the present inventor has demonstrated that the ten aforementioned ingredients can be satisfactorily analyzed within approximately 30 minutes or shorter analysis time per one cycle in the case of sequentially analyzing a large number of samples.

In the method for analyzing the active ingredients of cannabis according to the present invention, the first and second increase rates at which the mixture ratio of the phosphoric acid aqueous solution and phosphoric-acid-containing methanol is changed during the gradient elution, the relationship of the two rates as well as other conditions depend on the phosphoric acid concentration of each mobile phase, flow velocity of the mixed mobile phase, size of the column and other factors. In order to satisfactorily separate the ten aforementioned ingredients within approximately 30 minutes or shorter analysis time, the second increase rate should preferably be higher than the first increase rate, as stated earlier. Specifically, the second increase rate should preferably be approximately 3-4 times as high as the first increase rate.

In the method for analyzing the active ingredients of cannabis according to the present invention, an ODS column is used as the column. In an analysis using an ODS column, the particle size of the packing material, pore size of the particles and other related parameters of the ODS column affect the separation capability (e.g. theoretical plate number) and analysis time. Accordingly, in the method for analyzing the active ingredients of cannabis according to the present invention, an ODS column filled with a packing material having a particle diameter of 2.2 µm and particle-pore size of 8 nm may preferably be used as the column.

The use of the packing material whose particle size and pore size are smaller than those of a commonly used standard ODS column (with a particle size of 5 µm and pore size of 12 nm) makes it possible to realize a high theoretical plate number and satisfactorily isolate each ingredient while reducing the column length to shorten the analysis time.

In the method for analyzing the active ingredients of cannabis according to the present invention employs, an ultraviolet spectrometric detector or PDA detector, both being capable of directly detecting components in a solution (while maintaining the liquid form used as the detector. The detection wavelength of the detector may preferably be 220 nm.

The control program for a liquid chromatograph according to the present invention is a control program for controlling an operation of a liquid chromatograph including: a mobile phase mixer for regulating the mixture ratio of a first mobile phase and a second mobile phase; an injector for injecting a liquid sample into a mixed mobile phase prepared by the mobile phase mixer; a column for separating components contained in the injected liquid sample; and a detector for detecting a component in an eluate exiting from the column, so as to analyze a plurality of active ingredients contained in cannabis using this liquid chromatograph, the control program characterized by performing:

a) a sample injection step, in which the injector is operated so as to inject the liquid sample into the mixed mobile phase while the mobile phase mixer is controlled so that a mixture ratio of the first mobile phase which is the phosphoric acid aqueous solution and the second mobile phase which is phosphoric-acid-containing methanol is maintained in a predetermined state;

b) a gradient elution step, in which the mobile phase mixer is controlled so that, after the liquid sample is injected into the mixed mobile phase in the sample injection step, a mixture ratio of the second mobile phase is increased at a first increase rate for a predetermined period of time, and subsequently, the mixture ratio of the second mobile phase is increased at a second increase rate which is higher than the first increase rate.

The control program for a liquid chromatograph according to the present invention is a program for operating a computer (which may be a commonly used personal computer configured for control operations or dedicated computer embedded in the device) for controlling the mobile phase mixer, injector and other elements of a liquid chromatograph. This program should include a time program for the gradient elution showing the relationship between the mixture ratio of the mobile phases or the opening of a valve for achieving that mixture ratio and the passage of time. For example, such a program can be offered to users in a packaged form (e.g. CD-ROM or DVD-ROM) or through the Internet or similar communication lines.

The control computer built in or connected to a liquid chromatograph controls the operations of the relevant sections according to the control program for a liquid chromatograph according to the present invention. For example, in the mobile phase mixer, the openings of the solenoid valves for allowing the passage of the first and second mobile phases are individually regulated with the passage of time so as to send the column a mixed mobile phase in which the mixture ratio of the two mobile phases gradually changes. By combining such a gradient elution with an ODS column, a plurality of major ingredients contained in cannabis, or specifically, the ten aforementioned ingredients can be satisfactorily separated from each other.

Advantageous Effects of the Invention

With the method for analyzing the active ingredients of cannabis as well as a control program for a liquid chromatograph according to the present invention, it is possible to identify a plurality of major active ingredients contained in cannabis and determine their quantities by a single analysis using a liquid chromatograph which is comparatively inexpensive and easy to operate and manipulate. Therefore, a system for analyzing the active ingredients of cannabis can be constructed at a low cost. Users who have introduced such a system do not need to manually perform complex tasks, such as the determination of analysis conditions; after the introduction of the system, users can promptly perform an analysis with simple operations that do not require burdensome exercises. Since the identification and quantitative determination of major active ingredients can be precisely performed within a short analysis time, a highly reliable analysis result can be obtained with a high level of throughput.

DESCRIPTION OF EMBODIMENTS

Figure 1:
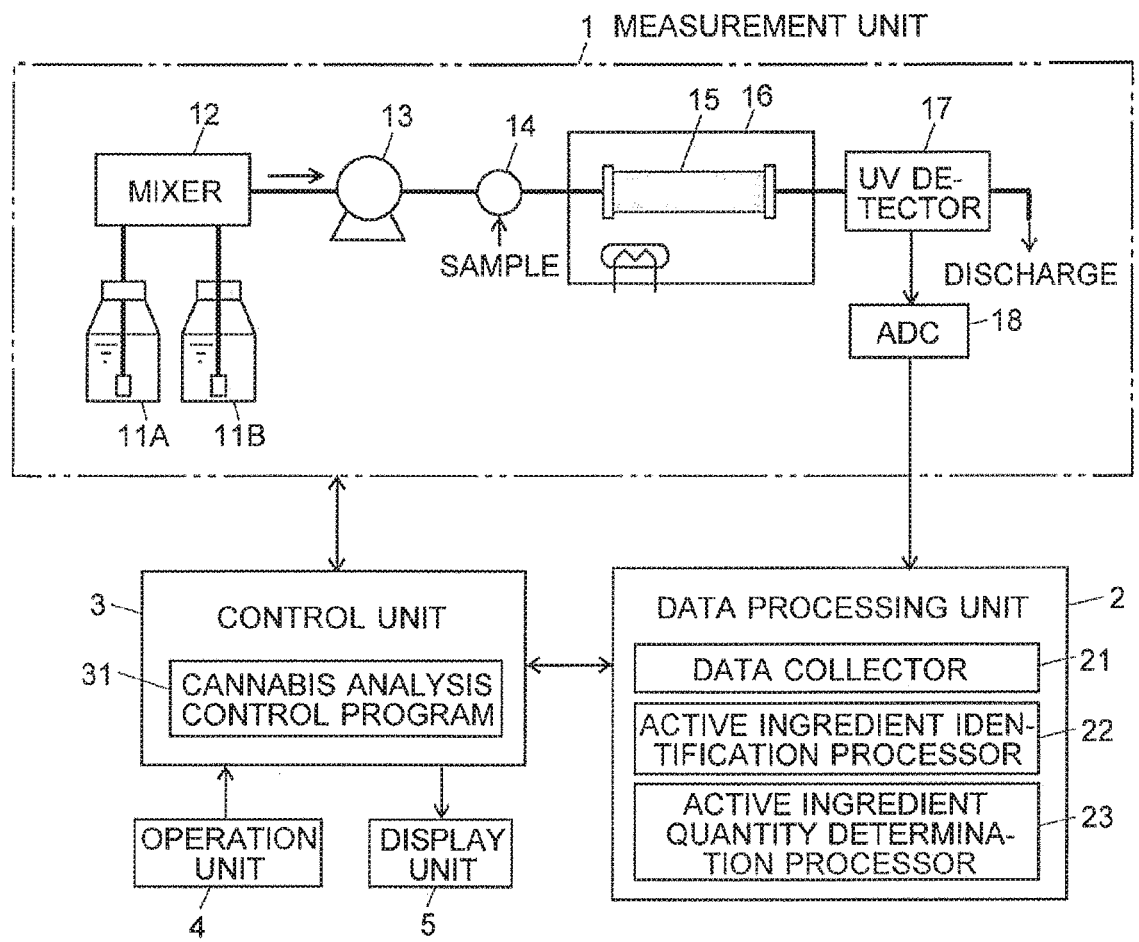
FIG. 1 is a schematic configuration diagram or one embodiment of an LC system for carrying out a method for analyzing the active ingredients of cannabis according to the present invention.

One mode of the method for analyzing the active ingredients of cannabis according to the present invention is described with reference to the attached drawings. FIG. 1 is a schematic configuration diagram of one embodiment of an LC system for carrying out the method for analyzing the active ingredients of cannabis according to the present invention.

As shown in FIG. 1, this LC system includes a measurement unit 1, data processing unit 2, control unit 3, operation unit 4 and display unit 5.

The measurement unit 1 is a high-performance liquid chromatograph (HPLC), which includes: mobile phase containers 11A and 11B which respectively hold different mobile phases (which are hereinafter called "mobile phases A and B"); a mixer 12 including a plurality of variable-opening solenoid valves for mixing the two mobile phases A and B at a predetermined mixture ratio; a liquid-sending pump 13 for drawing and supplying the mobile phases A and B from the mobile phase containers 11A and 11B, respectively, via the mixer 12; an injector 14 for injecting an amount of liquid sample into the mobile phase supplied from the liquid-sending pump 13; a column 15 for temporally separating the components (including active ingredients and foreign substances) in the injected liquid sample; a column oven 16 for controlling the temperature of the column 15; an ultraviolet spectrometric detector (UV detector) 17 for detecting a component in an eluate coming from the exit port of the column 15; and an analog-to-digital converter (ADC) 18 for sampling the detection signals from the ultraviolet spectrometric detector 17 at predetermined intervals of sampling time and for converting those signals into digital data.

The data processing unit 2 includes, as its functional blocks, a data collector 21, active ingredient identification processor 22, and active ingredient quantity determination processor 23. This unit processes the detection data obtained with the ultraviolet spectrometric detector 17 and digitized by the ADC 18, so as to identify active ingredients in the liquid sample and determine their quantities. The controller 3 has a built-in storage section, in which a cannabis analysis control program 31 is stored. According to this program, a CPU and other devices in the control unit 3 appropriately control relevant sections of the measurement unit 1 as well as the data processing unit 2 to perform analysis operations, which will be described later. The operation unit 4 allows operators (users) to command the control unit 3 to initiate the measurement or perform other operations. The display unit 5 is used to show analysis results and other kinds of information.

In the LC system of the present embodiment, a phosphoric acid aqueous solution is contained as mobile phase A in the mobile phase container 11A, while phosphoric-acid-containing methanol is contained as mobile phase B in the mobile phase container 11B. In the present embodiment, the concentration of the phosphoric acid aqueous solution is 0.085% (v/v). The concentration of the phosphoric-acid-containing methanol is also 0.083% (v/v).

The column 15 is an OSD column for the reversed-phase LC. In the present embodiment, the column has a length (L) of 75 mm and inner diameter (I.D.) of 3.0 mm. The particle size of the packing material is 2.2 μm. The particle-pore size is 8 nm. As a specific example, a column manufactured by Shimadzu Corporation under the name of "Shim-pack XR-ODS II" can be used as the column 15.

The ultraviolet spectrometric detector 17 has a detection cell through which the eluate is passed. A predetermined wavelength of light is cast into the eluate in the detection cell, and the intensity of the resultant transmitted light is detected to obtain, as the detection signal, the absorbance of light by the eluate. This ultraviolet spectrometric detector 17 may be an ultraviolet-visible spectrometric detector. A photodiode array detector may also be used in place of the ultraviolet spectrometric detector 17. In any case, a detector capable of directly detecting components in a solution is suitable, since a mobile phase which is a phosphoric-acid-containing solution is non-volatile; a detector which requires vaporization of the eluate is unsuitable in such a case.

The LC analysis conditions specified in the cannabis analysis control program 31 in the LC system of the present embodiment are as follows:

Flow velocity of the mobile phase: 1.0 mL/min
Gradient elution condition, in terms of the mixture ratio of mobile phase B: 60% (0-5 min)—72% (at 16 min)—95% (22-24 min)—60% (25-30 min)
Amount of injected liquid sample: 5 μL
Detection wavelength: 220 nm
Column oven temperature: 50° C.
Detector cell temperature: 40° C.

Figure 2:
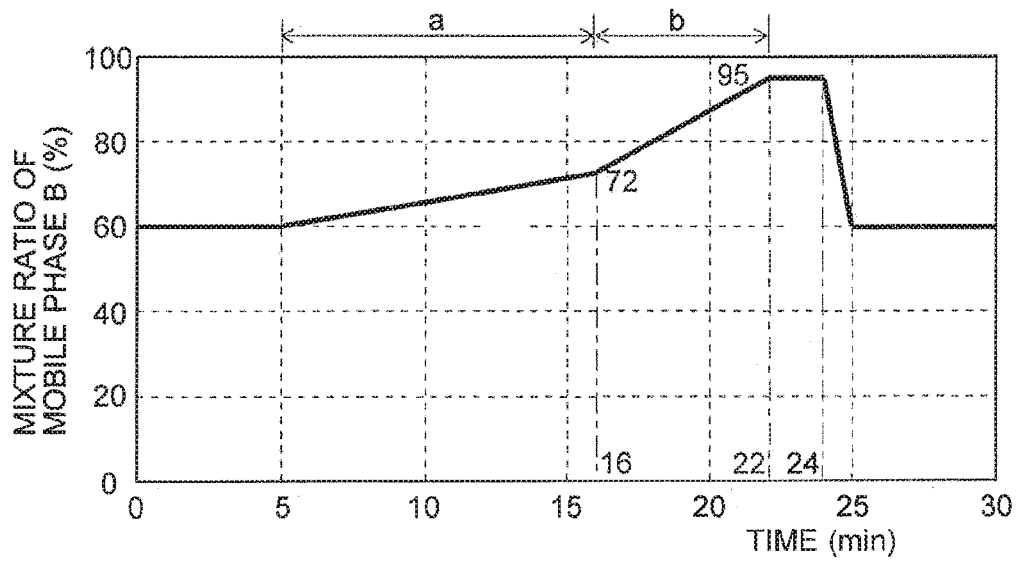
FIG. 2 is a diagram showing one example of the time program for the gradient elution in the LC system of the present embodiment.

FIG. 2 graphically shows the time program in the gradient elution condition. As shown in FIG. 2, the mixture ratio of mobile phase B is increased from 60% to 72% at a rate of approximately 1.1%/min for 11 minutes (period "a") after the elapsed time from the sample injection point (at 0 minutes) reaches 5 minutes until the elapsed time reaches 16 minutes. Subsequently, the mixture ratio of mobile phase B is increased from 72% to 95% at a rate of approximately 3.8%/min for 6 minutes (period "b") after the elapsed time from the sample injection point reaches 16 minutes until the elapsed time reaches 22 minutes. The increase rate of the mixture ratio of mobile phase B within period "b" is approximately 3.5 times as high as that of the mixture ratio of mobile phase B within period "a". In this manner, by changing the increase rate of the mixture ratio of mobile phase B in two stages so that the rate becomes higher in the second stage, a satisfactory capability of separating a plurality of active ingredients is ensured while the analysis time is made to be as short as possible.

The active ingredients of cannabis to be analyzed in the LC system of the present embodiment are the following ten ingredients: tetrahydrocannabivarin (THCV), cannabidiol (CBD), cannabigerol (CBG), cannabidiolic acid (CBDA), cannabigerolic acid (CBGA), cannabinol (CBN), Δ9-tetrahydrocannabinol (d9-THC), Δ8-tetrahydrocannabinol (d8-THC), cannabichromene (CBC), and Δ9-tetrahydrocannabinolic acid A (THCA-A). As already noted, no official method for the analysis of the active ingredients of cannabis is specified in the USA. Therefore, a study has been conducted to reveal what kinds of active ingredients are designated as analysis targets by major existing commissioned analytical institutions, and the ten aforementioned ingredients have been selected on the assumption that any active ingredient designated as an analysis target by three or more organizations should be considered to be a major active ingredient.

Next, a procedure for analyzing a sample in the LC system of the present embodiment is described.

As noted earlier, during the analysis, the control unit 3 controls the measurement unit 1 and data processing unit 2 according to the cannabis analysis control program 31. For example, when a command to initiate the measurement is issued from the operation unit 4, the control unit 3 receives this command and controls the mixer 12 so that mobile phases A and B are mixed at a predetermined initial mixture ratio (in the present example, 60% in terms of the mixture ratio of mobile phase B) while operating the liquid-sending pump 13 so that the flow velocity of the mixed mobile phase is maintained at the aforementioned value (in the present example, 1.0 mL/min). As a result, the mixed mobile phase having the aforementioned initial mixture ratio is supplied at a fixed flow velocity through the injector 14 to the column 15.

According to a command from the control unit 3, the injector 14 injects the aforementioned amount (5 μL) of liquid sample into the mobile phase at a predetermined timing. Simultaneously with the sample injection, the data collector 21 in the data processing unit 2 begins to collect data obtained by digitizing the detection signals of the ultraviolet spectrometric detector 17. The liquid sample injected from the injector 14 is carried into the column 15 by the flow of the mobile phase. While the sample is passing through the column 15, the components in the sample are temporally separated. The components separated in the column 15 sequentially exit from the exit port of the column 15 and pass through the detection cell of the ultraviolet spectrometric detector 17. The ultraviolet spectrometric detector 17 casts a predetermined wavelength (in the present example, 220 nm) of light into the eluate passing through the detection cell, detects the intensity of the resultant transmitted light, and obtains the absorbance of light by the eluate as the detection signal. This detection signal is digitized and stored in the data collector 21 as the detection data.

With the passage of time from the sample injection point, the control unit 3 regulates the openings of the solenoid valves in the mixer 12 according to the time program as shown in FIG. 2. Specifically, during the periods "a" and "b", the opening of the solenoid valve for mobile phase A is gradually decreased, while that of the solenoid valve for mobile phase B is gradually increased. Consequently, the mixture ratio of mobile phase B increases while the flow velocity is constantly maintained. As the mixture ratio of mobile phase B increases, the elution power becomes stronger. In this process, the elution power is not merely made to be gradually stronger; the elution power is changed at a higher rate in the second part of the analysis period than in the first part, so as to achieve both sufficient separation and accelerated elution of the components elated in the second part while ensuring a satisfactory degree of separation of the components eluted in the first part.

In practice, after the elution of the last one of the ten ingredients is completed within period "b", the concentration is reset from the final value (mixture ratio of 95%) to the initial value fixture ratio of 60%), and a sufficient length of equilibrium time is provided before the completion of one analyzing cycle.

The injector 14 allows for a continuous analysis in which a large number of prepared samples are sequentially injected into the mobile phase. In such a continuous analysis, the next analysis is subsequently performed after one analyzing cycle as just described is completed.

Figure 3:
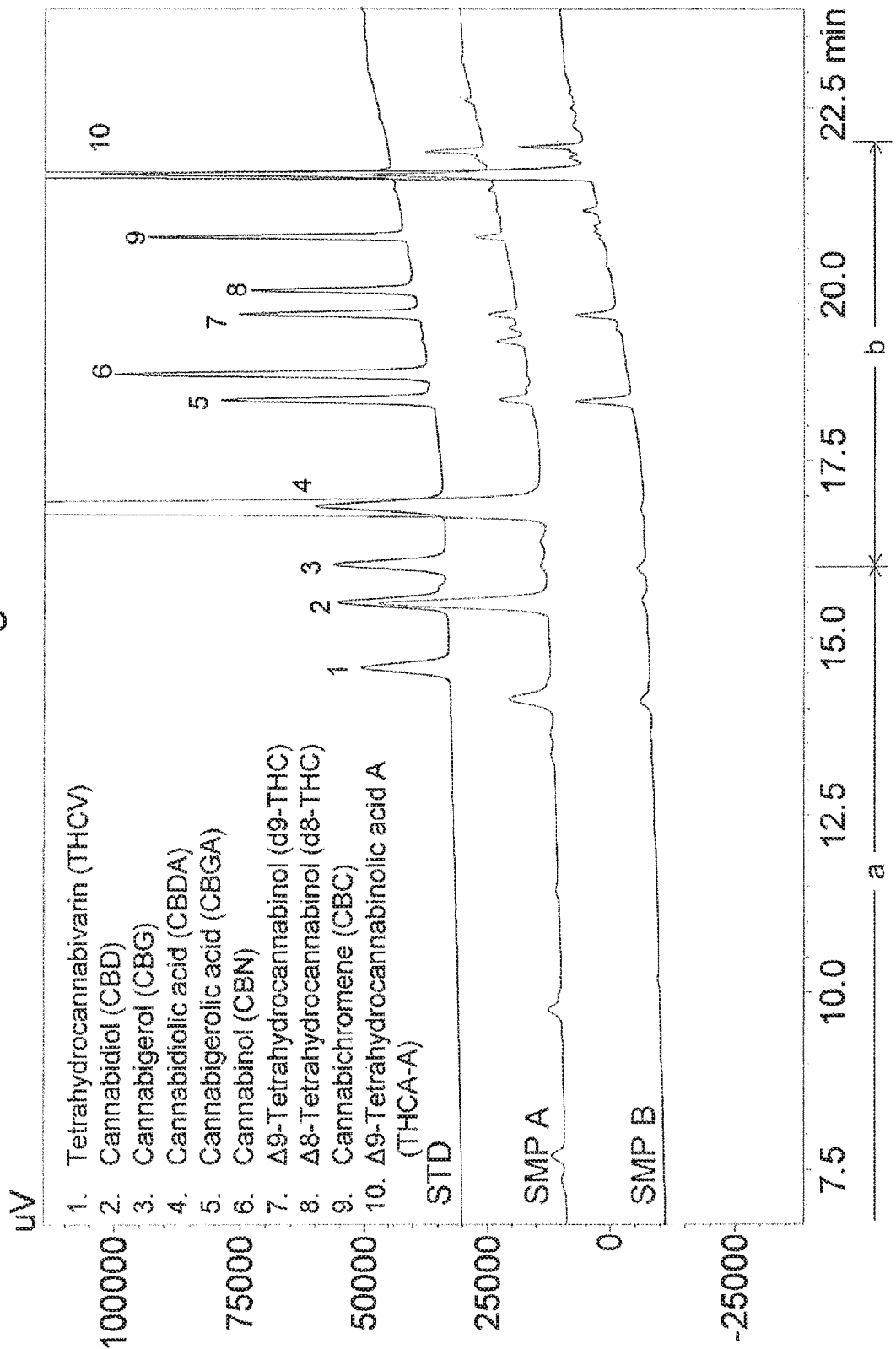
FIG. 3 is a graph showing measured examples of the chromatogram obtained by a measurement performed for a standard sample (STD) in which the ten major ingredients contained in cannabis were mixed, and for two real samples (SMP A and SMP B), using the LC system the present embodiment.

FIG. 3 is a graph showing measured examples of the chromatogram obtained by a measurement performed for a standard sample (STD) in which the ten aforementioned ingredients were mixed, and for two real samples (SMP A and SMP B), using the LC system of the present embodiment. Real sample SMP A was a corolla sample of cannabis which contained a high amount of Total CBD, while real sample SMP B was a corolla sample of cannabis which contained a high amount of Total THC. Needless to say, the standard sample contains no foreign substances other than the ten aforementioned active ingredients, while the real samples contain various foreign substances and other active ingredients different from the ten aforementioned active ingredients (those different active ingredients can also be regarded as foreign substances). Therefore, it is important to be capable of not only sufficiently separating the ten active ingredients from each other hut also sufficiently separating the ten active ingredients from other components.

As can be seen in the chromatogram of the standard sample in FIG. 3, the peaks which respectively correspond to the ten ingredients are sufficiently separated from their respective neighboring peaks. It can be seen that the peak which corresponds to d9-THC (No. 7) and one which corresponds to d8-THC (No. 8), which are particularly difficult to be separated, are also satisfactorily separated from each other.

In the chromatogram of real sample SMP A in FIG. 3, the peaks corresponding to the abundant ingredients, CBD and CBDA, are observed with high intensities at the same locations (retention times) as the peaks corresponding to CBD and CBDA on the chromatogram of the standard sample. By comparison, in the chromatogram of real sample SMP B in FIG. 3, the peak corresponding to the abundant ingredient, THCA-A, is observed with a high intensity at the same location (retention time) as the peak corresponding to THCA-A on the chromatogram of the standard sample. It can also be recognized that real samples SMP A and SMP B have additional peaks at different positions from the peaks corresponding to the ten aforementioned ingredients. The graph demonstrates that those additional peaks have also been satisfactorily separated from the peaks corresponding to the ten ingredients.

The data obtained by the analysis in the previously described manner are stored in the data collector 21 of the data processing unit 2. Accordingly, after the completion of or in the middle of the analysis, the active ingredient identification processor 22 creates a chromatogram as shown in FIG. 3 based on the obtained data, detects each peak on the chromatogram according to a predetermined algorithm, and compares the retention time of the peak with those of the ten previously registered active ingredients, to identify the component corresponding to that peak. A peak which does not correspond to any of the ten active ingredients may be judged as unidentified, or other libraries (or the like) may additionally be referenced to continue the compound identification process as extensively as possible. Meanwhile, for each ingredient which has been identified (i.e. whose presence has been confirmed) among the ten ingredients, the active ingredient quantity determination processor 23 computes the area value of the peak and calculates a quantitative value from the computed value with reference to a calibration curve included in the cannabis analysis control program 31. The control unit 3 displays the identification result and quantitative determination result on the display unit 5.

As shown in FIG. 3, the ten active ingredients as the analysis targets can be satisfactorily separated from each other, and the other foreign substances can also be satisfactorily separated from the ten active ingredients. Accordingly, it is possible to precisely identify each active ingredient based on its retention time, and to accurately determine the quantitative value of the identified ingredient.

An experiment conducted by the present inventor has confirmed that the analysis of the ten active ingredients can be successfully completed within 30 minutes or shorter analysis time by using the LC system of the previous embodiment. It has also been confirmed that an analysis according to the following specifications can be successfully performed:

Lower limit of quantitative determination: 0.7 mg/L or lower for all active ingredients.

Mutual separation of active ingredients: the degree of separation should be 1.8 or higher.

Separation of active ingredients from foreign substances originating from real sample: the degree of separation should be 1.2 or higher.

Linearity of calibration curve: the linearity contribution ratio ($R^2$) should be 0.999 or higher.

Carryover: the carryover of each active ingredient should be less than 0.1%.

The numerical values presented in the previous embodiment, such as the size of the column 15 and LC analysis conditions, are mere examples and can be appropriately changed.

The LC system of the previous embodiment has the ten aforementioned active ingredients designated as the analysis targets. Needless to say, some of those ingredients may be excluded from the analysis targets. The opposite is also naturally possible; i.e. other active ingredients or foreign substances which are separable from the ten active ingredients may additionally be identified along with the ten ingredients.

Furthermore, it is evident that the previous embodiment is a mere example of the present invention and can be appropriately changed or modified within the spirit of the present invention.

REFERENCE SIGNS LIST

1 . . . Measurement Unit
11A, 11B . . . Mobile Phase Container
12 . . . Mixer
13 . . . Liquid-Sending Pump
14 . . . Injector
15 . . . Column
16 . . . Column Oven
17 . . . Ultraviolet Spectrometric Detector (UV Detector)
18 . . . Analog-to-Digital Converter (ADC)
2 . . . Data Processing Unit
21 . . . Data Collector
22 . . . Active Ingredient Identification Processor
23 . . . Active Ingredient Quantity Determination Processor
3 . . . Control Unit
31 . . . Cannabis Analysis Control Program
4 . . . Operation Unit
5 . . . Display Unit

The invention claimed is:

1. A method for analyzing a plurality of active ingredients contained in cannabis using a liquid chromatograph, the method comprising:
   a) a separation step, in which a plurality of components contained in a liquid sample are separated from each other by gradient elution using an ODS column as a column, with a phosphoric acid aqueous solution and phosphoric-acid-containing methanol as mobile phases;
   b) a detection step, in which each component separated in the separation step is detected with a detector which is either an ultraviolet spectrometric detector or photodiode array detector; and
   c) an identification step, in which a plurality of predetermined active ingredients are identified based on retention times of peaks observed on a chromatogram created based on a detection result obtained in the detection step, wherein:
   the plurality of predetermined active ingredients to be identified include a following ten ingredients: tetrahydrocannabivarin (THCV), cannabidiol (CBD), cannabigerol (CBG), cannabidiolic acid (CBDA), cannabigerolic acid (CBGA), cannabinol (CBN), Δ9-tetrahydrocannabinol (d9-THC), Δ8-tetrahydrocannabinol (Δ8-THC), a cannabichromene (CBC), and Δ9-tetrahydrocannabinolic acid A (THCA-A); and
   a mixture ratio of the phosphoric-acid-containing methanol in the gradient elution in the separation step is changed so that the mixture ratio is increased at a first increase rate and subsequently at a second increase rate which is higher than the first increase rate.

2. The method for analyzing active ingredients of cannabis according to claim 1, wherein:
   at least two ingredients are separated from each other and sequentially eluted from the column within a period of time where the mixture ratio of the phosphoric-acid containing methanol is being increased at the first increase rate, whereas seven ingredients are separated from each other and sequentially eluted from the column within a period of time where the mixture ratio of the phosphoric-acid containing methanol is being increased at the second increase rate.

3. The method for analyzing active ingredients of cannabis according to claim 1, wherein:
   the second increase rate is 3-4 times as high as the first increase rate.

4. The method for analyzing active ingredients of cannabis according to claim 1, wherein:
   the column is an ODS column filled with a packing material having a particle diameter of 2.2 μm and a particle-pore size of 8 nm.

5. The method for analyzing active ingredients of cannabis according to claim 1, wherein:
   the detection wavelength of the detector is 220 nm.

6. A non-transitory computer-readable medium storing a control program for controlling an operation of a liquid chromatograph to perform the method of claim 1, the liquid chromatograph including: a mobile phase mixer for regulating a mixture ratio of a first mobile phase and a second mobile phase; an injector for injecting a liquid sample into a mixed mobile phase prepared by the mobile phase mixer; a column for separating components contained in the injected liquid sample; and a detector for detecting a component in an eluate exiting from the column, so as to analyze a plurality of active ingredients contained in cannabis using this liquid chromatograph, the control program characterized by performing:
   a) a sample injection step, in which the injector is operated so as to inject the liquid sample into the mixed mobile phase while the mobile phase mixer is controlled so that a mixture ratio of the first mobile phase which is the phosphoric acid aqueous solution and the second mobile phase which is phosphoric-acid-containing methanol is maintained in a predetermined state;
   b) a gradient elution step, in which the mobile phase mixer is controlled so that, after the liquid sample is injected into the mixed mobile phase in the sample injection step, a mixture ratio of the second mobile phase is increased at a first increase rate for a predetermined period of time, and subsequently, the mixture ratio of the second mobile phase is increased at a second increase rate which is higher than the first increase rate.

7. The computer-readable medium according to claim 6, wherein:
   the second increase rate is 3-4 times as high as the first increase rate.

8. The method for analyzing active ingredients of cannabis according to claim 2, wherein:
   the second increase rate is 3-4 times as high as the first increase rate.

9. The method for analyzing active ingredients of cannabis according to claim 2, wherein the at least two ingredients are THCV and CBD.

10. The method for analyzing active ingredients of cannabis according to claim 2, wherein the seven ingredients are CBDA, CBGA, CBN, d9-THC, d8-THC, CBC and THCA-A.

* * * * *